United States Patent [19]

Nath

[11] 4,149,086
[45] Apr. 10, 1979

[54] UV IRRADIATION DEVICE

[76] Inventor: Guenther Nath, Speyererstrasse 21, Munich, Fed. Rep. of Germany

[21] Appl. No.: 916,419

[22] Filed: Jun. 16, 1978

Related U.S. Application Data

[63] Continuation of Ser. No. 771,137, Feb. 23, 1977, abandoned.

[30] Foreign Application Priority Data

Feb. 26, 1976 [DE] Fed. Rep. of Germany ....... 2607249
Nov. 2, 1976 [DE] Fed. Rep. of Germany ....... 2650209

[51] Int. Cl.$^2$ .............................................. G01J 1/00
[52] U.S. Cl. ................................... 250/504; 250/493
[58] Field of Search ................................ 250/504, 493

[56] References Cited

U.S. PATENT DOCUMENTS

| 2,267,834 | 12/1941 | Mulvany | 250/504 |
| 3,101,411 | 8/1963 | Richards | 250/504 |
| 3,712,984 | 1/1973 | Lienhard | 250/504 |

Primary Examiner—Harold A. Dixon
Attorney, Agent, or Firm—Edwin E. Greigg

[57] ABSTRACT

The specification describes an irradiation device, more particularly for use for causing the polymerization of fillings of resins in dentistry, using radiation in the UVA range which is transmitted from a radiation source via a light guide. The source of UVA radiation is a tungsten incandescent filament lamp with a color temperature of at least 3150° K. and an electrical power of at least 15 Watts. For a defined solid angle, which is not less than 6 sterad, the radiation from the filament of the lamp is collected by an UV reflecting reflector and focussed at a focal point $F_1$ lying outside the incandescent filament lamp. In the ray path between the filament of the lamp and the focal point $F_1$ a dielectric thin film reflection filter is provided with a defined angle alpha of inclination $\neq 0°$ of the filter normal to the optic axis defined by the incandescent filament and the focal point $F_1$. This thin film filter has a maximum reflection capacity for radiation which is incident at the angle alpha to the filter normal in a wavelength range between 330 nm and 400 nm. The reflecting thin film filter produces a second focal point $F_2$ which lies outside the optic axis as mentioned above and is substantially less intensive with respect to the radiation power density. This second, less intensive focal point comprises a comparatively high fraction of UVA radiation. The radiation collected at the point $F_2$ is subjected to further optical filtration to remove undesired visible and infrared radiation either by reflecting thin film filters or by absorption filters or by the internal filter action of the light guide employed. The UVA radiation which converges at the second point $F_2$ is collected by a light guide whose effective numerical aperture is larger than 0.34.

15 Claims, 9 Drawing Figures

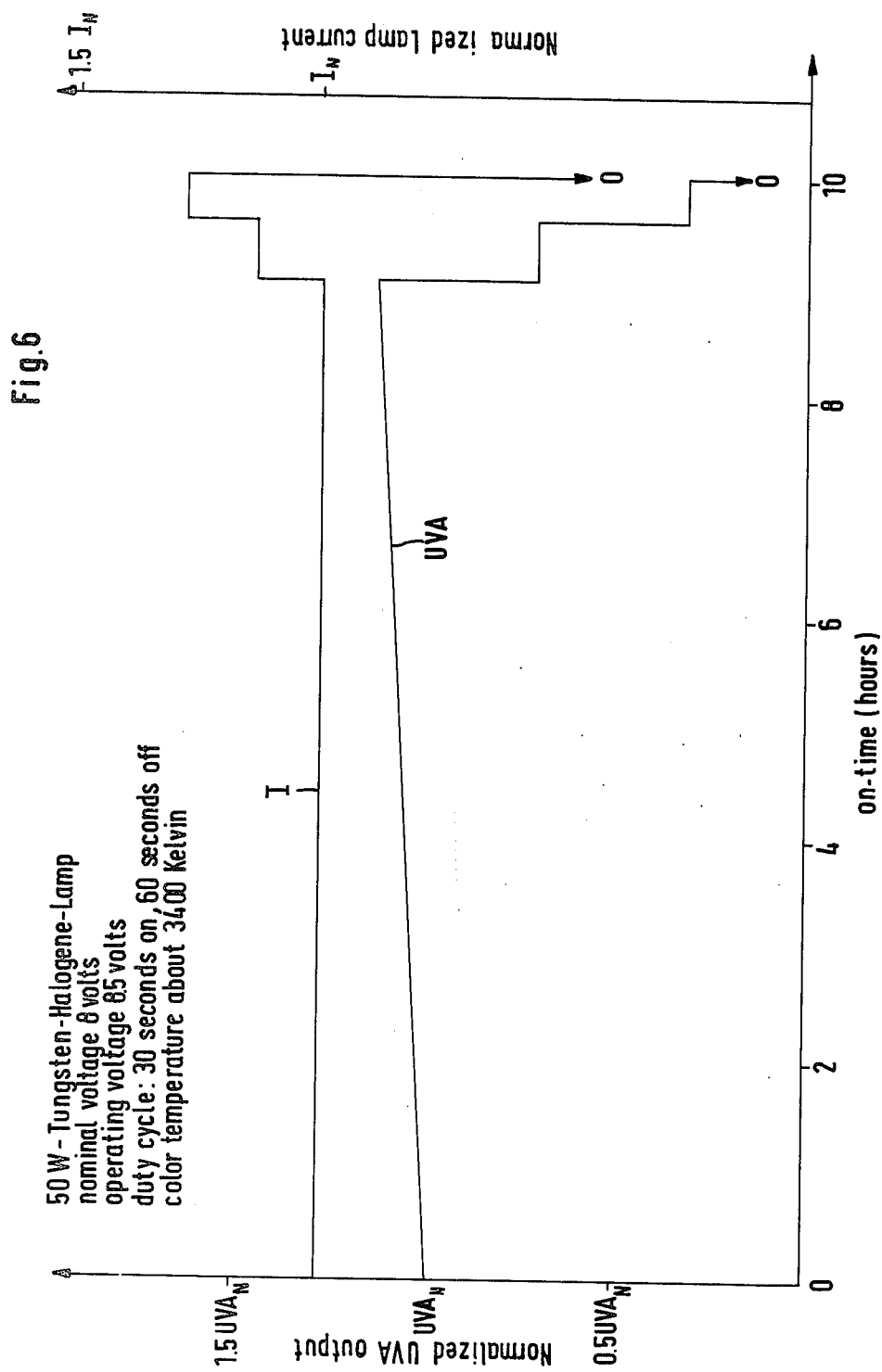

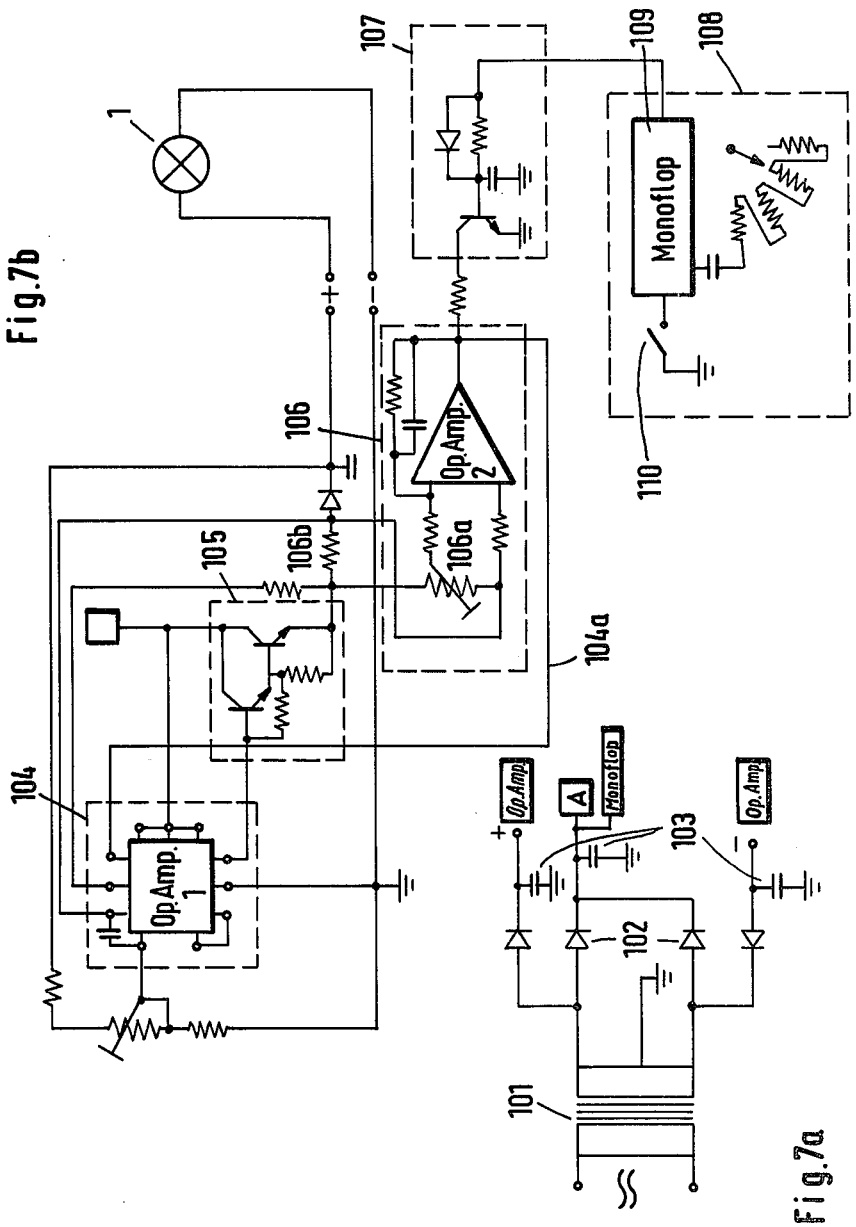

UV IRRADIATION DEVICE

CROSS-REFERENCE TO RELATED APPLICATIONS

This application is a continuation of patent application Ser. No. 771,137 entitled UV IRRADIATION DEVICE filed Feb. 23, 1977 by the applicant herein now abandoned.

BACKGROUND OF INVENTION

1. Field to which Invention Relates

The invention relates to an irradiation device for the ultraviolet range of the spectrum and more specifically for the UVA spectral range, that is to say for the wavelength range from 300 nm to 420 nm and consisting of a radiation source and a light guide.

2. The Prior Art

Such irradiation devices are used more specifically in dentistry in order to use UVA radiation for the polymerisation of dental resins, which are used for prevention, restoring and orthodontal purposes.

For such applications in the dental field, more especially for applications in situ the UVA irradiation device must comply with the following criteria.

1. The radiation intensity in the UV range must be sufficiently high in order to ensure, to take an example, that a wafer of composite material (for example Nuva Phil) with a diameter of 6 mm and a depth of 2 mm with a white or white-yellowish coloration cures satisfactorily within a period of radiation of 30 seconds at the most. The radiation intensity necessary for this purpose in the effective UVA range (wavelength lambda between 320 nm and 400 nm) should in this respect amount to at least 20 mW/cm$^2$.

2. The radiation intensity should remain as constant as possible during the effective life of the UVA radiation source, since this will ensure that the same polymerisation time applies for the polymerisation of the same volume of composite material. This property is particularly important since if the UVA intensity decreases, complete and thorough curing and the durability of a dental filling cannot be guaranteed.

3. The UVA radiation source should immediately be ready for use after switching on, that is to say its full UVA power should be emitted and it should be capable of being switched on immediately directly after being switched off. This property makes it possible for the dentist to use the equipment in the most rational manner.

4. In no case should the UVA irradiation device emit radiation in a wavelength range below 320 nm as otherwise erythma and in some cases even malignant tissue changes may be inflicted on the patient and the dentist treating him. This criterion has in the United States of America even been made part of a statutory provision for such UVA irradiation devices by the Food and Drugs Administration. The constructional safety of the irradiation device should therefore be of such a high standard that even in the case of damage to the device no radiation escapes lying below 320 nm.

5. The UVA radiation source should have a low cost price as owing to its limited peiod of life it must be regarded as an expendable part of the irradiation device.

Irradiation devices which comprise an UV lamp and a rigid or flexible light guide have already been used in dentistry and are furthermore described in the following patent specifications by way of example: German (Offenlegungsschrift) No. 2,315,721, (Patentschrift) 2,206,424, Swiss Pat. No. 530,798 and U.S. Pat. No. 3,638,312.

Prior art irradiation devices comprise a gas discharge lamp as the UV light source as for example a mercury vapor discharge lamp. As UVA light guides transparent to UVA use is made of rigid light guides of quartz glass or flexible quartz fibre bundles and also liquid-plastics light guides.

These known irradiation devices leave much to be desired as regards their practical utility.

While known irradiation devices provide a sufficiently high UVA intensity for polymerisation, especially owing to the use of a gas discharge lamp as a light source they have the following disadvantageous properties. After operation for approximately 100 hours there is a substantial decrease in the UVA output, this applying particularly for the 365 nm Hg-line which is important for the polymerisation. After several hundred hours of operation the UVA output may have dwindled to only a third of the original amount. This leads to substantially longer polymerisation times. A further disadvantage of these known UVA irradiation devices resides in that the Hg lamps require a heating time of several minutes and after being switched off can only be struck again after a pause of a few minutes. Although measures have been proposed to accelerate the evaporation of mercury and accordingly to reduce the warm up time of a Hg high pressure lamp to approximately 20 seconds, such measures are technically involved and expensive. In the case of most devices with a Hg lamp the dentist must keep the device continuously in a ready state and the actual period of use only amounts to a very small fraction of the time which the device is actually switched on. A consequence of this is that after only a few hours of effective use time the UVA intensity substantially decreases.

Gas discharge lamps, more particularly Hg lamps, also have an intensive emission below 320 mm. This radiation must be cut out by means of external filters and the housing for the lamp must therefore be designed so as to be fully radiation-tight, something which makes it more difficult to remove dissipated heat. This latter circumstance applies more particularly for manually held irradiation devices with a rigid light guide. Damage to the radiation filter, which is generally arranged in front of the light entrance face of the light guides can lead to the emission of hard UV radiation without this being noticed. Finally it is to be mentioned that the gas discharge lamps as used in the case of prior art devices have a very high cost price.

SHORT SUMMARY OF THE INVENTION

One aim of the invention is therefore that of providing an UVA irradiation device which can both be manipulated manually, that is to say in conjunction with a rigid light guide, and can also be employed in conjunction with a flexible UVA light guide with an external radiation source, the device avoiding the disadvantages as mentioned above.

A preferred embodiment of the invention is characterised in that as an UVA radiation source use is made of a tungsten incandescent filament lamp with a color temperature of at least 3150° K. and an electrical power of at least 15 Watts, in that a defined spatial angle amount, which is however not below 6 sterad, of the radiation emitted from the incandescent filament of the lamp, is collected by an UV reflecting reflector and is focussed on a focal point $F_1$ lying outside the incandescent filament lamp, in that in the ray path between the incandescent filament of the lamp and the focussing point $F_1$ a dielectric thin layer reflection filter is located which with a defined inclination angle $\alpha \neq 0°$ of slant of the filter normal to the optic axis $W-F_1$ defined by the incandescent filament and the focussing point $F_1$, in that this thin layer filter has the highest possible reflecting capacity for radiation which is incident at the angle $\alpha$ to the filter normal in the wavelength range of 330 nm to 400 nm, in that the reflecting thin layer filter produces a second focal point $F_2$, which lies outside the optic axis $W-F_1$ and is substantially less intensive as regards the radiation power density and this focal point $F_2$ contains a comparatively high UVA radiation power density and in that the radiation collected at the point $F_2$ is subjected to further opticl filtration to remove the residual undesired visible and infrared radiation, that is to say either by reflecting thin film filters or by absorption filters or by the internal filtration action of the light guide employed, and in that the UVA radiation collected at the point $F_2$ is accepted by a light guide, whose effective numerical aperture exceeds 0.34. (The numerical aperture is defined as $\sqrt{n_1^2 - n_2^2}$, in which $n_1$ is the reflective index of the light conducting core and $n_2$ is the reflective index of the insulating optically thinner medium.)

In order to achieve the highest possible UVA yield or output and also to comply with VDE (Verein Deutscher Elektroingenieure) safety regulations concerning low voltages in medical equipment held in the hand, it is appropriate to use a tungsten halogen lamp as a tungsten incandescent filament lamp. Such lamps allow maximum color temperatures of up to 3400° K. and in the case of the switching on times coming into question here of approximately 20 to 30 seconds for curing a dental filling the halogen cycle makes itself felt because it leads to improved consistency in the UVA emission of the lamp.

LIST OF SEVERAL FIGURES OF THE DRAWINGS

In what follows embodiments of the invention will be described with reference to the accompanying drawings and further features and advantages of the invention will be discussed.

FIG. 1a shows an enlarged view of a part of the device in accordance with FIG. 1;

FIG. 6 is a graph of the lamp current and UVA emission of the lamp as a function of the duration of operation of the lamp in hours; and FIGS. 7a and 7b show circuit diagrams of a preferred regulated lamp power unit.

DESCRIPTION OF PREFERRED EMBODIMENTS OF THE INVENTION

Figure 1:
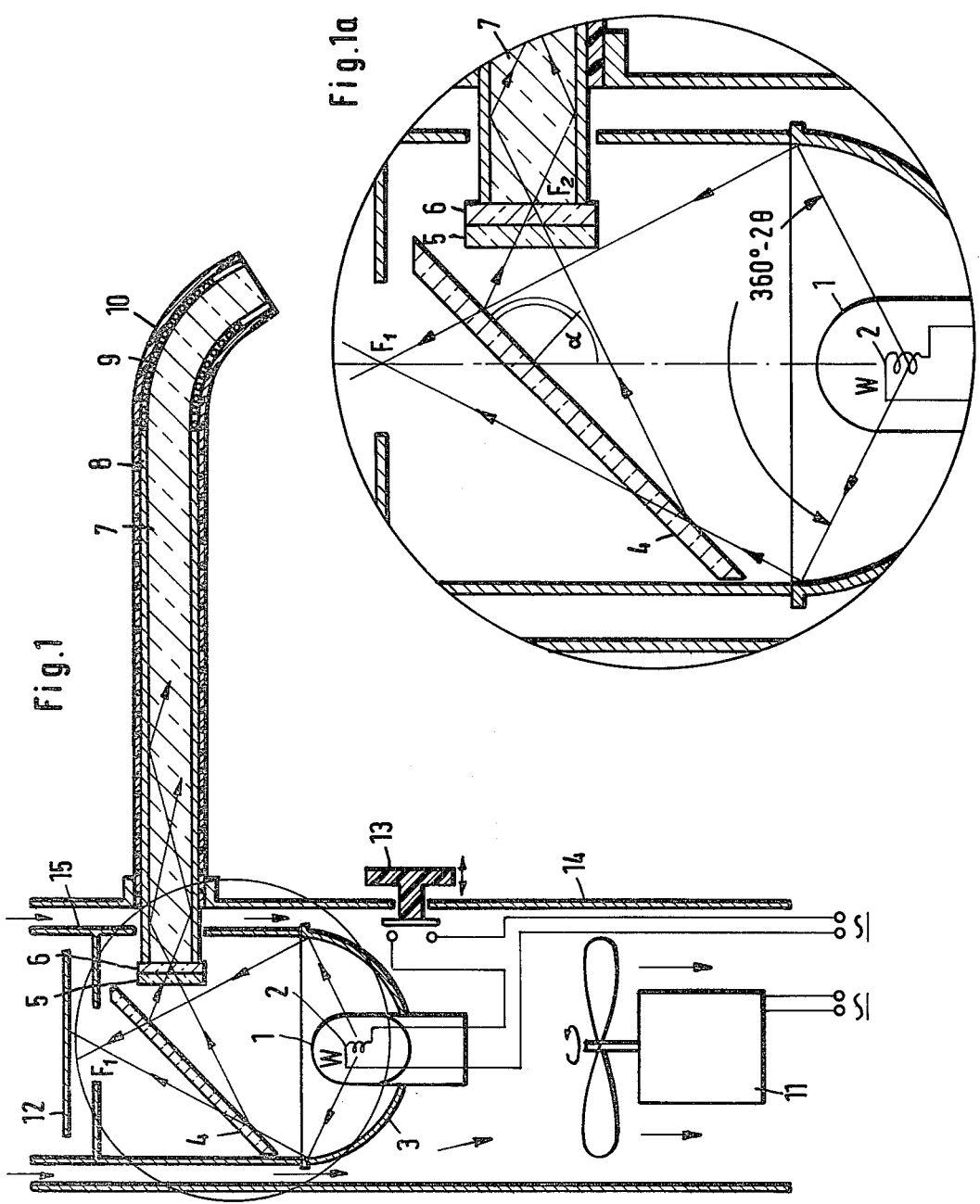
FIG. 1 is a diagrammatic representation of one embodiment of an irradiation device in accordance with the invention for manual manipulation.
Figure 2:
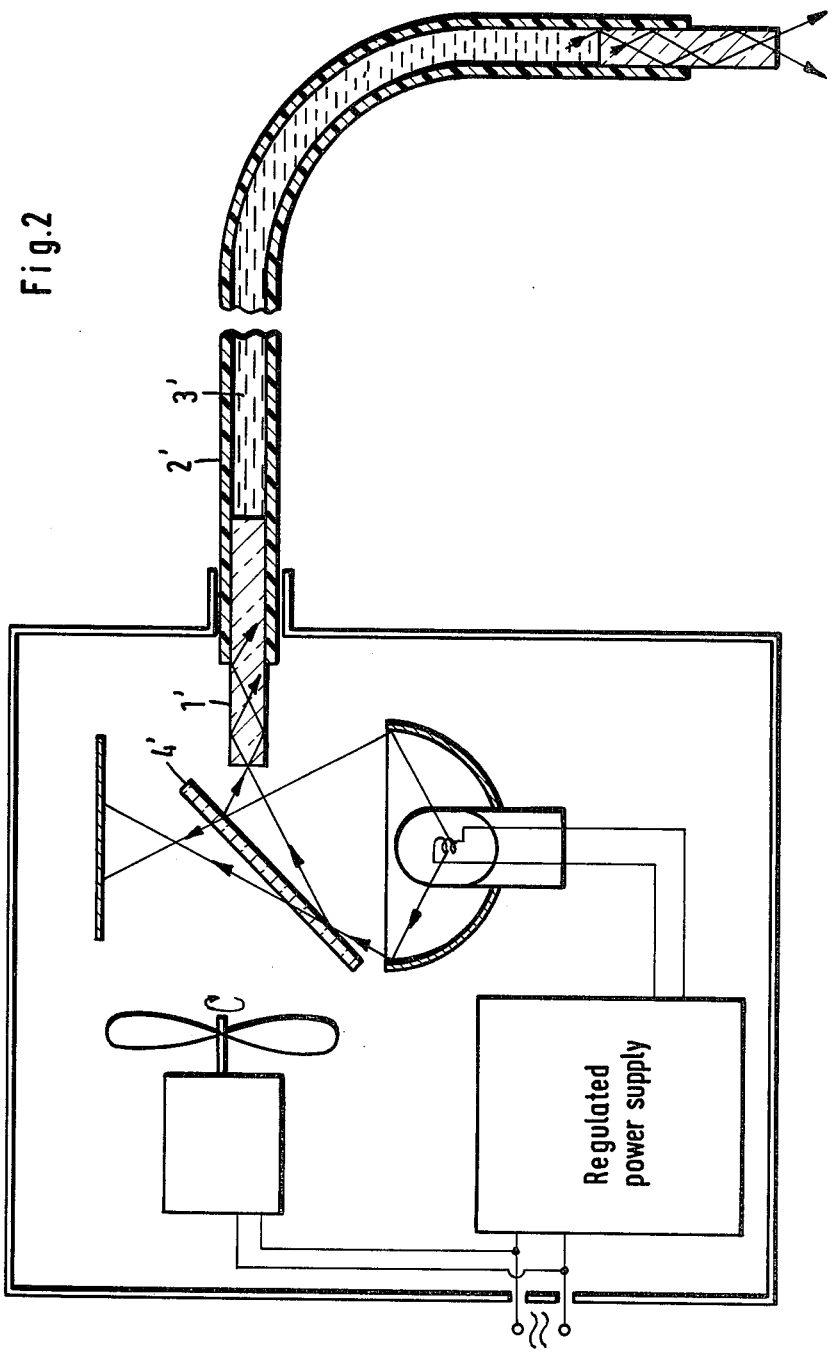
FIG. 2 shows diagrammatically a view of a second embodiment of the invention with a flexible light guide.

In the case of the UVA irradiation devices in accordance with the invention as a light source use is made of an incandescent filament lamp, preferably a tungsten halogen lamp. For UVA irradiation devices for manual manipulation of the type indicated in FIG. 1 halogen lamps with an electrical rated or nominal input power between 20 and 75 Watts and preferably 50 Watts have been found acceptable, while the halogen lamp employed in the case of stationary devices having a flexible light guide of the type specified in FIG. 2 preferably have an electrical rated input power of 150 to 200 Watts. In the case of a practical form of construction the halogen lamp is located in an aluminum reflector, which has the geometrical form of an ellipsoid of rotation, in whose one focal point the incandescent filament W of the halogen lamp is located and which accepts the radiation emitted by the filament in a solid angle $\Omega$ of approximately 9 sterad and which focusses it at a focal point $F_1$. ($\Omega = 2\pi(1-\cos\theta)$, see FIG. 1a. Between the halogen lamp 1 and the focus $F_1$ there is a dielectric thin film filter at a slant to the axis $W-F_1$, which has a high degree of reflection in the wavelength range between approximately 340 and 420 nm and in the remaining range has a high transmission coefficient and focusses the reflected UVA-rich radiation in a second focal point $F_2$. The diameter of the focusses is in each case preferably between 3 and 7 mm and the full divergence of the radiation in the focal points is between 40° and 80°. The dielectric thin film filter 4 in the case of the arrangement shown in FIGS. 1 and 2 is subject to a very high thermal loading and owing to the constant switching on and switching off of the lamp is subject to repeated changes in temperature, since approximately 70% of the electrical power pervades the filter in the form of radiation. As a durable substrate for the filter 4 it has been found in the present application that quartz glass is more particularly suitable. However other thermally resistant glasses could be used for this purpose as for example commercially available Vycor glass. The thin film filter is preferably flat. The angle $\alpha$ of the filter normal to the optic axis $W-F_1$ can lie between 10° and 80° and conveniently between 25° and 65° through the preferred value is 45°. The position of the second focal point $F_2$ defined by the thin film filter is preferably in the center of the light entrance face of a light guide which is so arranged that the optic axis of the light guide 7 makes a right angle to the axis $W-F_1$.

Figure 4:
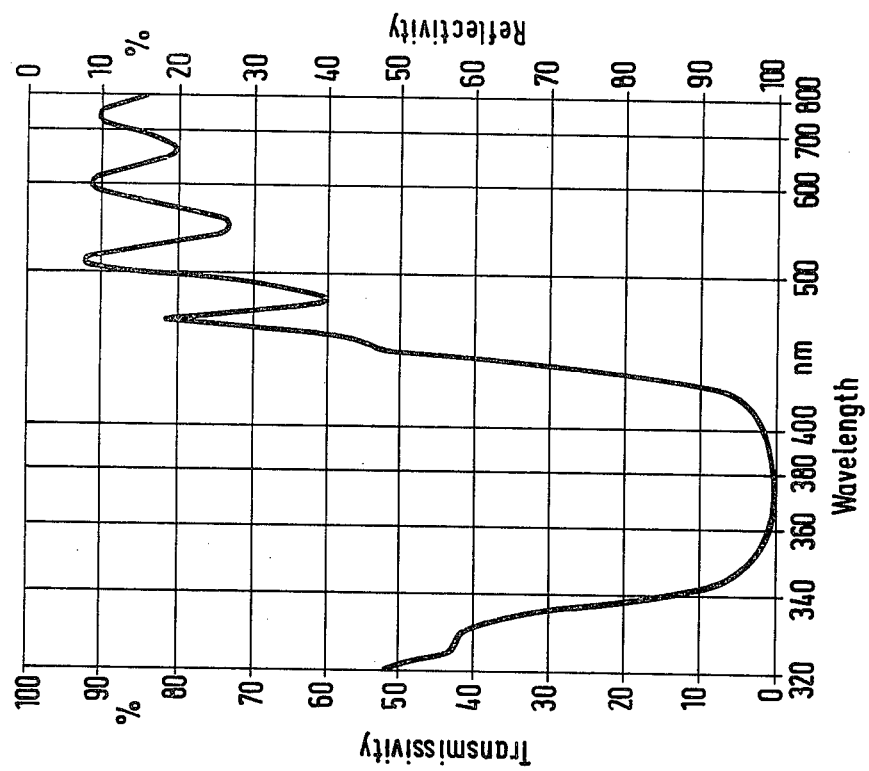
FIG. 4 is a graph of the transmission and reflection characteristics of a preferred optical filter.

The reflecting properties of a thin film filter as accepted in practise for radiation, which impinges at an angle of 45° to the filter normal is represented in FIG. 4. For radiation which impinges in the angle range of 45° ± 30° to the filter normal the reflection curve is displaced somewhat towards the shorter wavelengths. The reflection coefficient R should lie above 80% and preferably above 90% in the range of the spectrum of 340 to 410 nm applicable for polymerisation. For a wavelength not greater than $\pi$ 320 nm owing to erythma formation at least R should be not greater than 50% and the transmission coefficient T should not be less than 50% and owing to the undesired dazzle and heating effects of non-useful visible and infrared radiation for a wavelength not less than $\lambda$ 450 nm at least R should not exceed 60% and T should be not less than 40% and preferably however R should not exceed 30% and T should not be less than 70%.

In practise such a reflection filter brings about an attenuation of the undesired visible and infrared radiation by a factor of six to eight, something which considerably reduces the possibility of tissue damage owing to radiation searing, but heating effects and optical dazzle of the radiation reflected by the thin film filter and conducted by the light guide is still too intensive. This applies more especially for manual devices, in the case of which the light guide preferably consists of a homogeneous quartz rod 7 which is optically isolated by air and is bent down at the light exit end. Such a rod 7 has a diameter of approximately 6 to 10 mm and a length of approximately 20 cm. Therefore further filtration of the radiation is necessary in order to eliminate vestiges of visible and infrared radiation. This further filtration can however, owing to the strong attenuation of the radiation by the reflection filter, be carried out by a commercially available KG + BG or KG + UG filter glass combination without the danger of thermal overheating of such transmission filters which absorb undesired radiation. With such a filter combination it is possible to achieve an output power of the radiation emitted by the light guide of only 200 mW, there being no substantial dazzle and heating effects in this case.

In the case of the construction in form of a table-top device (see FIG. 2) the arrangement of further separate filters in addition to the reflection filter 4' can be dispensed with if a liquid-plastics light guide is used as a flexible light guide as described in the German patent specification (Offenlegungsschrift) No. 2,404,424, which achieves the desired filtering action by the addition of the dyestuff to the light conducting liquid.

Figure 3:
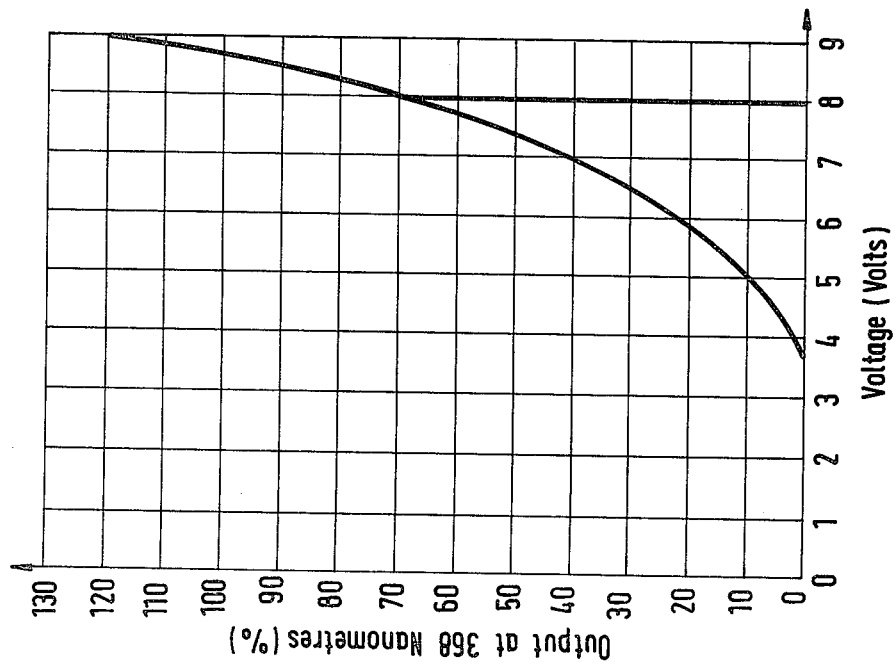
FIG. 3 shows a graph of the light output power at 368 mm from a tungsten halogen incandescent lamp as a function of the operating voltage.

The UVA radiation power or output emitted by the halogen light varies to a disporportionally large extent on changes in the lamp power. FIG. 3 shows how very sensitively the UVA yield, measured in a narrow spectral range around 365 nm, varies with the full voltage. The rated voltage of the 50 Watt halogen lamp amounts in this case to 8 Volts. Since variations in the line voltage and therefore of the stepped-down lamp voltage of ± 10% may certainly be expected, the UVA yield would vary by + 48% and − 37% with respect to the UVA output at the nominal voltage. Furthermore, in order to provide a sufficient UVA yield for polymerisation, the halogen lamps should not be operated below the rated voltage and it is better to operate them at 3 to 12% above the rated voltage so that the color temperature of the filament is as high as possible. A halogen lamp only operated with a transformer could accordingly be fused when the line voltage increases owing to variations. In order to achieve the highest possible, constant UVA yield and for safety reasons for the lamp it is therefore preferred to stabilize the power supply of the lamp to avoid line variations. For reasons of economy a stabilization of the lamp supply voltage to ± 5% departure from the rated voltage can be sufficient. In this case the UVA yield varies by ± 20%, something which can just be tolerated, if one takes into account that the speed of polymerisation only varies in accordance with the square root of the radiation intensity. The stabilization of the supply voltage of the halogen lamp can, in a conventional manner, be ensured by electronic or electrical measures. Preferably it is not only the voltage but also the current which is regulated, as will be described below with reference FIGS. 5 to 7b.

In technology the practical utility of a tungsten halogen lamp which has a comparatively low output and can therefore be manipulated by hand, in dentistry for the polymerisation in situ of dental resins has apparently so far been overlooked. All devices which are commercially available operate with mercury vapor lamps and more modern developments envisage the use in addition of a pulsed xenon gas discharge lamp with a complicated power supply.

However I have been able to show experimentally that in the case of an optimum optical arrangement making use more particularly of an UV reflector with a very large spatial angle (Ω above 6 steread) and a light guide with a maximum numerical aperture, it is possible to make use of the very small UVA radiation, emitted by a halogen lamp, for in situ polymerisation in a manner which complies with safety regulations, and as a result to achieve cure times and degrees of hardness which are not inferior to those achieved with known devices with a comparable electrical power.

The arrangement of the optic axis of the light guide and of the reflector at an angle to each other ensures maximum patient safety both with respect to hard UV radiation and also as regards intensive heat radiation which might be feared if the filter 4 and the filter 5, 6 should break or be damaged. In the case of a co-linear arrangement of the optic axes of the reflector 3 and the light guide 7 and using a 50 Watt halogen lamp on breakage of the filter a radiation power, principally infrared radiation, would be emitted from the light guide amounting to approximately 10 Watts, something which could lead to signs of cauterization of the patient. In the case of the arrangement at an angle in accordance with FIG. 1 breakage of the filter only leads to the emission from the light guide of power which exceeds the normal power by an amount which is not dangerous (for example only 1.5 Watts instead of 200 mW on breakage of the filters 5 and 6) or on breakage of the filter 4 no power at all will be emitted.

The use of a tungsten halogen lamp offers a substantial further safety factor as compared with a mercury lamp in as far as the filtration out of radiation with a wavelength not exceedings λ 320 nm (FDA Regulation) does not offer any problems, since at a wavelength not exceeding 320 nm the lamp hardly has any substantial emission. A strong tendency to produce erythma and the production of ozone are therefore not to be feared.

As regards instantaneous switching on and switching off the halogen lamp offers a substantial advantage with respect to a mercury lamp. Troublesome strike times and lost time on re-striking do not occur. The dentist can therefore work more rapidly and rationally.

Tungsten halogen lamps with an electrical power of 50 Watts and a high efficiency reflecting elliptoid aluminum reflector, which covers a spatial angle of approximately 9 steread from the radiation source are commercially available and are produced on a large scale for cine and slide projectors at an economic price. Such lamps can be used for example for the manual device represented in FIG. 1 and are substantially less costly than corresponding mercury lamps.

A further decisive advantage of the tungsten halogen lamp is the constancy of the UVA emission with time. Thus a 50 Watt halogen lamp showed a decrease in the UV emission of only 5% after carrying out 1500 polymerisiations each lasting 30 seconds. By way of comparison a mercury high pressure lamp with a power of 100 Watts showed a decrease in the UVA emission (at a wavelength of 365 nm) of 35% after 1500 polymerisations each lasting 30 seconds.

The following example will show the suitability of tungsten halogen lamps for polymerisation:

The manual device of FIG. 1 in the case of a practical embodiment, not to be interpreted for limitation, comprise the following components:

Lamp: 50 Watts, 8 V
Reflector: elliptoid aluminum reflector = 9 steread
Filters: thin layer filter in accordance with FIG. 4, slant 45° to the optic axis
Filter 5: KG 3, thickness 2 mm,
Filter 6: BG 1, thickness 2 mm
Light guide: homogeneous quartz rod length 20 cm, diameter 8 mm
UVA output power: 45 mW (wavelength between 320 and 405 nm equivalent to 90 mW/cm².

A wafer of commercially available UV sensitized methyl methacrylate composite material (Nuva Phil, L) with a diameter of 6 mm and a layer thickness of 2 mm could be completely cured after 20 seconds of irradiation. This curing time is acceptable in dentistry and is not longer than is the case with commercially available devices using mercury lamps. Furthermore hardness of the polymer is comparable with the hardness produced by Hg lamps.

The embodiment shown in FIG. 1 of the manually manipulated UVA irradiation device is constructed in the following manner.

The 50 Watt 8 V halogen lamp 1 with a filament 2 is located in the focal point of an aluminum reflector in the form of an ellipse of rotation. The reflector 3 has a spatial angle of approximately 9 steread. The lamp 1 is switched on and off by means of a manual switch 13. The dielectric thin film filter 4 on a quartz glass substrate is pervaded by the radiation focussed at a reflector and the focal point $F_1$ with an angle $\alpha$ of 45° of the filter normal to the optic axis $W-F_1$ (see FIG. 1a).

The UVA radiation comprised in the ray cone is reflected by the reflection filter 4 together with visible and infrared radiation, which however only makes up approximately 13% of the intensity of the radiation transmitted through the filter, on to the light entrance face of the light guide 7 into the point $F_2$. Two absorption filters 5 and 6 (KG and BG filters) free the radiation which is to be used substantially of vestiges of infrared and visible radiation. The light transmitted through the filter 4 impinges on a heat shield 12. Instead of the heat shield it is also possible to use a filter transparent to red and infrared in order to allow the heat radiation to emerge from the device without any dazzle effect, something which leads to a lower heating effect. A fan 11 or another cooling device, for example a connection with a pressurized gas source for producing a cooling air flow in the housing, is however generally necessary in order to be able to hold the device over extended periods of time in the hand without excessive heating. The device is shown in FIG. 1 generally true to scale and has a cylindrical shape with an outer tube 14 with a diameter of approximately 5 cm and an inner tube 15, which represents the actual radiation chamber. The light guide 7 is preferably a homogeneous quartz rod which is bent at the outlet end and it is journalled for turning about an axis coinciding with its straight part. In its straight part it is clad with a metal tube 8 and in its curved part it is clad with a plastics or metal spiral member 9. A shrunk on tube 10 is arranged on the spiral member 9 and the tube 8 in order to achieve a homogeneous surface. The cladding of the curved optical light guide part, which is only isolated from the air, with the spiral member 9 ensures particularly low light losses. The shrunk on foil 10 does not make contact with the light guide rod while the spiral member only lies on the non-isolated light rod with a comparatively small area of contact. FIG. 1a indicates the geometrical relationships of the optical arrangement of FIG. 1. In particular the angle $\alpha$ of slant of the filter normal to the optic axis of the reflector is represented, together with the complement of the angle 2 $\theta$ as 360°, for which the spatial angle $\Omega = 2 \pi (1-\cos \theta)$ can be calculated for the reflector.

In another arrangement, the same results of the invention are obtained by locating the dielectric thin film filter 4 in the path of the radiation of the filament W. By way of example, the dielectric thin film filter 4 may be combined with the optical focusing means or concave reflector 3. In such an arrangement, the filter 4 divides up the filament radiation into first and second components, the first component, rich in radiation in the UVA range, being directed into the light guide 7 as in the embodiment of FIG. 1.

The table-top device in accordance with FIG. 2 operates using the same optical principle as the manual device shown in FIG. 1. The tungsten halogen lamp preferably has a higher rated power of for example 150 Watts at 15 Volts as a rated voltage. The UVA radiation is focussed via the reflection filter as is the case with FIG. 1 on the radiation entrance face of a liquid/plastics light guide. This light guide has a particularly high transmission coefficient in the UVA range and has a light guiding core, which consists of an aqueous ionic solution, which is optically isolated by means of a flexible tube 2' of tetrafluoroethylenehexafluoropropylene copolymer.

As compared with a quartz fibre bundle light guide this light guide has a substantially higher effective numerical aperture, which is well adapted to the aperture angle of the aluminum reflector. In this case additional filters in addition to the filter 4' are not necessary, since the light guiding liquid 3' of the guide can be so colored that it absorbs visible and infrared radiation. FIG. 2 also shows the regulated power pack for the lamp supply.

As already mentioned above the filament voltage of the tungsten halogen lamp, which preferably lies above the rated voltage in order to attain a high UVA yield, should be stabilized to protect it against variations in the line voltage and thus increase the length of life of the lamp. Furthermore current surges should be avoided as otherwise usually occur on switching on if the cold filament is immediately subjected to the whole operational voltage. This undesired current characteristic I' with the switching on surge is shown in FIG. 5.

It has furthermore been found that the operating current I of the lamp and the UVA radiation output power vary as a function of the duration of switching on of the lamp generally as indicated in FIG. 6. At the end of the life of the lamp the lamp current thus increases step by step, something which is accompanied by a corresponding decrease in the UVA output power. These changes are apparently caused by sudden changes in shape and concomitant changes in the temperature distribution in the tungsten helix.

Figure 5:
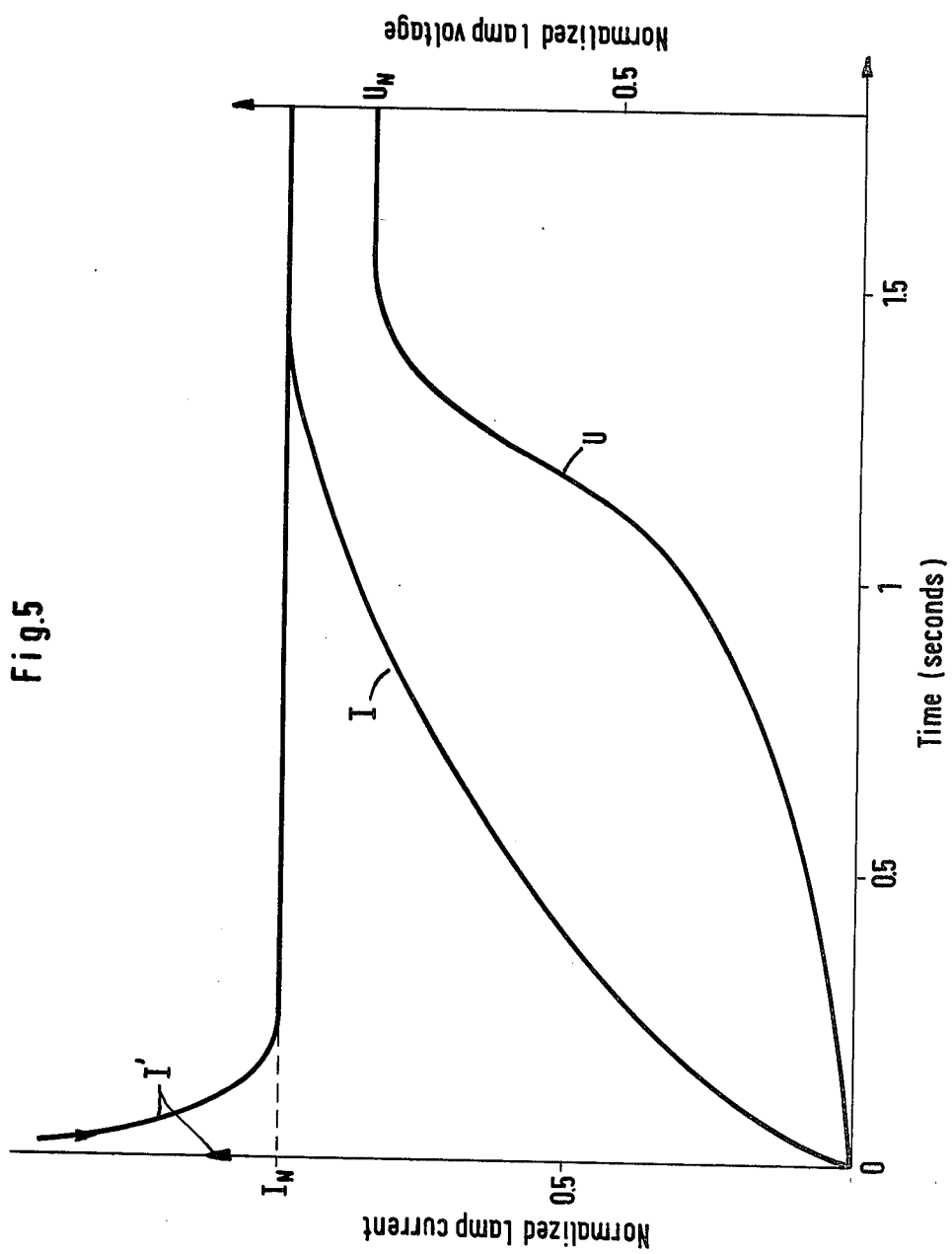
FIG. 5 is a graph showing the unregulated and, respectively, regulated lamp current and regulated lamp voltage following switching on of the lamp as a function of time.

It has been found that the length of life of the tungsten halogen lamp 1 in the UV irradiation devices described can be substantially increased if the operating current $I_B$ and the operating voltage $U_B$ are so controlled that they correspond to the curves in FIG. 5. The lamp current $I_B$ and the lamp voltage $U_B$ therefore rise comparatively slowly in accordance with a plain curve after switching on to reach their steady end values $I_N$ and $U_N$ respectively, after a certain period of time which is preferably greater than 0.3 and less than approximately 10 to 15 seconds. Particularly appropriate values for this period of time lie between 0.8 and 3 seconds.

The undesired stepped decay in the UVA yield, which may result in a possibly unnoticed and extremely undesirable reduction in the degree of polymerisation, is preferably cut out by providing the power pack for the lamp with an electronic sensor arrangement, which interrupts the power supply to the lamp when the lamp current rises by more than 10% above the operating current value $I_N$ of the lamp when new or if the ohmic resistance of the filament sinks below more than 10% on the basis of the initial value.

FIGS. 7a and 7b show an embodiment of a power supply circuit for the tungsten halogen lamp 1 of the UV irradiation device in accordance with the invention. Instead of the electronic voltage stabilizing circuit employed in this power pack it is naturally also possible to use other voltage stabilizers as for example conventional transformers with a saturable core (transductors).

The power pack in accordance with FIG. 7 comprises the following functional groups:

A line transformer 101, whose secondary is connected with a rectifying circuit 102 with a smoothing circuit 103;

a voltage regulator 104 of conventional construction, which comprises an operational amplifier Op.Amp. 1, which is supplied with a current ideal value signal via a line 104a and controls a power transistor circuit 105, which is in series with the circuit of the lamp 1;

a switch off logic system 106, which interrupts the lamp current when the latter rises for more than a certain percentage, for example 10 to 20 above the value of a new lamp. This switch off logic system comprises a second operational amplifier Op.Amp. 2, whose inputs are connected via a potentiometer circuit 106a with a current tapping resistor 106b, which is in series with the lamp current circuit. Between the summing input and the output of the operational amplifier a parallel RC member is connected;

a delay circuit 107 with an RC member and a transistor, which produces the function of the current $I_B$ shown in FIG. 5, and an adjustable timer 108, which comprises a monostable circuit 109 for programming the irradiation times with typical time settings of for example 10, 20, 30, 40, 50 and 60 seconds. The use of such a timer is appropriate in the present case since the switch off logic system 106 and the stabilization of the energy supply of the lamp ensure a very high degree of evenness in the UVA output power of the irradiation device accompanied by reproducible polymerisation times. An irradiation cycle is started by a switch 110, which can be actuated by the push button 13 (FIG. 1).

The curves in accordance with FIG. 6 were plotted for a tungsten halogen lamp with a rated or nominal power of 50 Watts and rated voltage of 8, which was operated with a voltage of 8.5 and was switched on for 30 seconds at a time and switched off for 60 seconds at the time. The sudden changes in current, which occurred at end of the life of the lamp, were probably due to short circuiting of adjacent coils of the tungsten helix.

What I claim is:

1. An UV irradiation device comprising an incandescent filament lamp with an electrical rated input power of at least 15 Watts, an electrical energy source for supplying the lamp, in a manner allowing switching on and switching off, with such a voltage that the incandescent filament in operation emits radiation with a color temperature of at least 3150° K., an optical focussing means, which collects the radiation from the filament of the lamp in a solid angle of at least 6 sterad of emitted radiation to a beam converging to a focal point, a dielectric thin film filter arranged in the path of the convergent beam and which divides up the convergent beam into a first component beam, which is relatively rich in radiation in the wavelength range between approximately 330 nanometer and approximately 400 nanometer (UVA range), and a second component beam, which is relatively rich in visible and infrared radiation, and the first and the second component beams converge at a first and a second component beam focus respectively, an elongated light guide which is transparent for the UVA radiation, having a light exit end and a light entrance end, which has an effective numerical aperture above 0.34 and is arranged at the first component beam focus in such a manner that the first component beam enters the light guide, an optical filter arrangement, the arranged in the path of the first component beam, for further reduction of the visible and infrared radiation still comprised in the first component beam, a light-tight housing, which encompasses the lamp, the focussing means, the filters and the light entrance end of the light guide, and a device for producing a forced cooling air circulation through the interior of the housing.

2. An irradiation device in accordance with claim 1, characterised in that the lamp is a tungsten halogen low voltage lamp.

3. An irradiation device in accordance with claim 1 or claim 2, characterised in that the thin film filter is a dielectric thin film reflection filter, which has a high reflection capacity for UVA radiation and has a high transmission capacity for radiation in the remaining spectral range and in that the thin film filter and the light entrance end of the light guide are so arranged that the connecting line between the filament of the lamp and the focal point makes an angle between 10 and 80° with the normal to the filter plane and the first component beam, rich in UVA radiation, is reflected into the light entrance end of the light guide.

4. An irradiation device in accordance with claim 3, characterised in that the filter arrangement comprises at least one transmission filter, which absorbs the visible or infrared radiation and is arranged in front of the light entrance end of the light guide and in that the light guide consists of a quartz rod.

5. An irradiation device in accordance with claim 3, characterised in that the light guide comprises a plastics flexible tube filled with an UV transparent liquid and in that the optical filter arrangement comprises a dyestuff dissolved in the liquid.

6. An irradiation device in accordance with claim 3, characterised in that the angle between said connecting line and filter normal lies between 40 and 50° and preferably amounts to about 45°.

7. An irradiation device in accordance with claim 1, characterised in that the focussing means comprises a concave mirror.

8. An irradiation device in accordance with claim 1, characterised in that the light guide comprises a quartz rod with a bent end, in that the quartz rod is arranged in a plastics tube and in that between the quartz rod and the plastics tube a spacing arrangement is located which, in the vicinity of the bent part of the quartz rod consists of a metal or plastics helix.

9. An irradiation device in accordance with claim 1, characterised in that the energy source supplies a regulated operating voltage to the lamp, which is up to 20% higher than the rated voltage of the lamp.

10. An irradiation device in accordance with claim 1 (or claim 9,) characterised in that the electrical energy source on switching on provides a current rising in accordance with a substantially plain function to an operating value.

11. An irradiation device in accordance with claim 10, characterised in that within a period of 0.3 to 3 seconds following switching on the current rises to the operational value.

12. An irradiation device in accordance with claim 1, characterised in that the electric energy source comprises a circuit arrangement which interrupts the current supplied to the lamp when the operating current of the lamp exceeds the value which is more than 5% above the operating current value when the lamp is new.

13. An irradiation device in accordance with claim 1, characterised in that the device for producing forced circulation of cooling air comprises a fan arranged in the interior of the housing.

14. An irradiation device in accordance with claim 1, characterised in that the device for producing forced circulation of cooling air comprises a connection for a pressurized gas supply.

15. An UV irradiation device comprising an incandescent filament lamp with an electrical rated input power of at least 15 Watts,
an electrical energy source for supplying the lamp, in a manner allowing switching on and switching off, with such a voltage that the incandescent filament in operation emits radiation with a color temperature of at least 3150 K, an optical focussing means, which collects the radiation from the filament of the lamp in a solid angle of at least 6 sterad of emitted radiation to a beam coverging to a focal point,
a dielectric thin film filter arranged in the path of the radiation of the filament and which divides up the radiation into a first component, which is relatively rich in radiation in the wavelength range between approximately 330 nanometer and approximately 400 nanometer (UVA range), and a second component, which is relatively rich in visible and infrared radiation, the first component converging at a first component focus,
an elongated light guide which is transparent for the UVA radiation, having a light exit end and a light entrance end, which has an effective numerical aperture above 0.34 and is arranged at the first component focus in such a manner that the first component enters the light guide, an optical filter arrangement, aranged in the path of the first component, for further reduction of the visible and infrared radiation still comprised in the first component,
a light-tight housing, which encompasses the lamp, the focussing means, the filters and the light entrance end of the light guide, and
a device for producing a forced cooling air circulation through the interior of the housing.

* * * * *